(12) United States Patent
Fonseca et al.

(10) Patent No.: US 7,481,771 B2
(45) Date of Patent: *Jan. 27, 2009

(54) IMPLANTABLE WIRELESS SENSOR FOR PRESSURE MEASUREMENT WITHIN THE HEART

(75) Inventors: Michael Fonseca, Atlanta, GA (US); Mark Allen, Atlanta, GA (US); David Stern, Grayson, GA (US); Jason White, Atlanta, GA (US); Jason Kroh, Villa Rica, GA (US)

(73) Assignee: CardioMEMS, Inc., Atlanta, GA (US)

( * ) Notice: Subject to any disclaimer, the term of this patent is extended or adjusted under 35 U.S.C. 154(b) by 396 days.

This patent is subject to a terminal disclaimer.

(21) Appl. No.: 10/886,829

(22) Filed: Jul. 7, 2004

(65) Prior Publication Data
US 2005/0015014 A1    Jan. 20, 2005

Related U.S. Application Data

(63) Continuation of application No. 10/054,672, filed on Jan. 22, 2002, now Pat. No. 6,855,115.

(51) Int. Cl.
*A61B 5/0215* (2006.01)
(52) U.S. Cl. .......................... 600/486; 607/60
(58) Field of Classification Search .................. 600/488, 600/486, 587, 407, 412, 421, 422, 431, 485, 600/552, 553, 561, 420; 607/60, 156; 324/652
See application file for complete search history.

(56) References Cited

U.S. PATENT DOCUMENTS

| | | | |
|---|---|---|---|
| 2,796,863 A | 6/1957 | von Wittern | |
| 3,867,950 A | 2/1975 | Fischell | |
| 3,942,382 A | 3/1976 | Hok | |
| 3,958,558 A | 5/1976 | Dunphy et al. | |
| 4,026,276 A | 5/1977 | Chubbuck | |

(Continued)

FOREIGN PATENT DOCUMENTS

CA    1 158 061    6/1983

(Continued)

OTHER PUBLICATIONS

A. Dehennis, K.D. Wise; "A Passive-Telemetry-Based Pressure Sensing System"; NSF Engineering Research Center For Wireless Integrated MicroSystems; Department of Electrical Engineering and Computer Science; The University of Michigan, Ann Arbor, MI 48109-2122 US.

(Continued)

*Primary Examiner*—Kennedy J Schaetzle
(74) *Attorney, Agent, or Firm*—Kilpatrick Stockton LLP

(57) ABSTRACT

The progress of a endovascular cardiac repair can be monitored by inserting a pressure transducer sensor using a catheter into a chamber of the heart during endovascular repair and then using a small, hand-held read out device to measure pressure easily, safely, inexpensively and accurately. In one aspect a sensor is introduced into the body by the steps of folding or rolling the sensor into a cylinder, loading it into a catheter, and deploying into the heart chamber by allowing it to unroll or unfold, either by itself or facilitated by the incorporation of a super-elastic alloy component.

32 Claims, 7 Drawing Sheets

U.S. PATENT DOCUMENTS

| | | |
|---|---|---|
| 4,127,110 A | 11/1978 | Bullara |
| 4,206,762 A | 6/1980 | Cosman |
| 4,207,903 A | 6/1980 | O'Neill |
| RE30,366 E | 8/1980 | Rasor et al. |
| 4,237,900 A | 12/1980 | Schulman et al. |
| 4,354,506 A | 10/1982 | Sakaguchi et al. |
| 4,378,809 A | 4/1983 | Cosman |
| 4,485,813 A | 12/1984 | Anderson et al. |
| 4,494,950 A | 1/1985 | Fischell |
| 4,521,684 A | 6/1985 | Gilby et al. |
| 4,596,563 A | 6/1986 | Pande |
| 4,713,540 A | 12/1987 | Gilby et al. |
| 4,718,425 A | 1/1988 | Tanaka et al. |
| 4,796,641 A | 1/1989 | Mills et al. |
| 4,815,472 A | 3/1989 | Wise et al. |
| 4,846,191 A | 7/1989 | Brockway et al. |
| 4,890,623 A | 1/1990 | Cook et al. |
| 4,899,752 A | 2/1990 | Cohen |
| 4,913,147 A | 4/1990 | Fahlstrom et al. |
| 4,934,369 A | 6/1990 | Maxwell |
| 4,987,897 A | 1/1991 | Funke |
| 5,113,868 A | 5/1992 | Wise et al. |
| 5,115,128 A | 5/1992 | Cook |
| 5,129,394 A | 7/1992 | Mehra |
| 5,131,399 A | 7/1992 | Sciarra |
| 5,165,289 A | 11/1992 | Tilmans |
| 5,181,423 A | 1/1993 | Philipps et al. |
| 5,192,314 A | 3/1993 | Daskalakis |
| 5,207,103 A | 5/1993 | Wise et al. |
| 5,265,606 A | 11/1993 | Kujawski |
| 5,353,800 A | 10/1994 | Pohndorf et al. |
| 5,367,376 A | 11/1994 | Lagakos et al. |
| 5,373,852 A | 12/1994 | Harrison et al. |
| 5,411,551 A | 5/1995 | Winston et al. |
| 5,431,171 A | 7/1995 | Harrison et al. |
| 5,440,300 A | 8/1995 | Spillman, Jr. |
| 5,487,760 A | 1/1996 | Villafana |
| 5,497,099 A | 3/1996 | Walton |
| 5,515,041 A | 5/1996 | Spillman, Jr. |
| 5,535,752 A | 7/1996 | Halperin et al. |
| 5,538,005 A | 7/1996 | Harrison et al. |
| 5,551,427 A | 9/1996 | Altman |
| 5,566,676 A | 10/1996 | Rosenfeldt et al. |
| 5,583,474 A | 12/1996 | Mizoguchi et al. |
| 5,593,430 A | 1/1997 | Renger |
| 5,600,245 A | 2/1997 | Yamamoto et al. |
| 5,626,630 A | 5/1997 | Markowitz et al. |
| 5,686,841 A | 11/1997 | Stolarczyk et al. |
| 5,695,155 A | 12/1997 | Macdonald et al. |
| 5,702,427 A | 12/1997 | Ecker et al. |
| 5,703,576 A | 12/1997 | Spillman, Jr. et al. |
| 5,713,917 A | 2/1998 | Leonhardt et al. |
| 5,722,414 A | 3/1998 | Archibald et al. |
| 5,723,791 A | 3/1998 | Koch et al. |
| 5,743,267 A | 4/1998 | Nikolic et al. |
| 5,796,827 A | 8/1998 | Coppersmith et al. |
| 5,807,265 A | 9/1998 | Itoigawa et al. |
| 5,836,886 A | 11/1998 | Itoigawa et al. |
| 5,860,938 A | 1/1999 | Lafontaine et al. |
| 5,899,927 A | 5/1999 | Ecker et al. |
| 5,935,084 A | 8/1999 | Southworth |
| 5,942,991 A | 8/1999 | Gaudreau et al. |
| 5,967,986 A | 10/1999 | Cimochowski et al. |
| 6,015,386 A | 1/2000 | Kensey et al. |
| 6,015,387 A | 1/2000 | Schwartz et al. |
| 6,019,729 A | 2/2000 | Itoigawa et al. |
| 6,024,704 A | 2/2000 | Meador et al. |
| 6,025,725 A | 2/2000 | Gershenfeld et al. |
| 6,030,413 A | 2/2000 | Lazarus |
| 6,033,366 A | 3/2000 | Brockway et al. |
| 6,053,873 A | 4/2000 | Govari et al. |
| 6,076,016 A | 6/2000 | Feierbach |
| 6,111,520 A | 8/2000 | Allen et al. |
| 6,113,553 A | 9/2000 | Chubbuck |
| 6,134,461 A | 10/2000 | Say et al. |
| 6,140,740 A | 10/2000 | Porat et al. |
| 6,159,156 A | 12/2000 | Van Bockel |
| 6,198,965 B1 | 3/2001 | Penner et al. |
| 6,201,980 B1 | 3/2001 | Darrow et al. |
| 6,206,835 B1 | 3/2001 | Spillman et al. |
| 6,229,190 B1 | 5/2001 | Bryzek et al. |
| 6,237,398 B1 | 5/2001 | Porat et al. |
| 6,239,724 B1 | 5/2001 | Doron et al. |
| 6,277,078 B1 | 8/2001 | Porat et al. |
| 6,278,379 B1 | 8/2001 | Allen et al. |
| 6,287,253 B1 | 9/2001 | Ortega et al. |
| 6,373,264 B1 | 4/2002 | Matsumoto et al. |
| 6,400,974 B1 | 6/2002 | Lesho |
| 6,409,674 B1 | 6/2002 | Brockway et al. |
| 6,442,413 B1 | 8/2002 | Silver |
| 6,454,720 B1 | 9/2002 | Clerc et al. |
| 6,645,143 B2 | 11/2003 | Van Tassell et al. |
| 6,667,725 B1 | 12/2003 | Simons et al. |
| 6,682,490 B2 | 1/2004 | Roy et al. |
| 6,765,493 B2 | 7/2004 | Lonsdale et al. |
| 6,855,115 B2 * | 2/2005 | Fonseca et al. ............... 600/488 |
| 6,923,769 B2 | 8/2005 | Nishii et al. |
| 6,926,670 B2 | 8/2005 | Rich et al. |
| 6,939,299 B1 * | 9/2005 | Petersen et al. ............. 600/398 |
| 2002/0077556 A1 | 6/2002 | Schwartz |
| 2002/0151816 A1 | 10/2002 | Rich et al. |
| 2002/0188207 A1 | 12/2002 | Richter |
| 2003/0031587 A1 | 2/2003 | Hu et al. |
| 2003/0136417 A1 | 7/2003 | Fonseca et al. |
| 2003/0139677 A1 | 7/2003 | Fonseca et al. |
| 2004/0122494 A1 | 6/2004 | Eggers et al. |
| 2005/0075697 A1 | 4/2005 | Olson et al. |
| 2005/0085703 A1 | 4/2005 | Behm |
| 2005/0154321 A1 | 7/2005 | Wolinsky et al. |

FOREIGN PATENT DOCUMENTS

| | | |
|---|---|---|
| DE | 196 44 858 5 | 10/1996 |
| EP | 0257801 | 3/1988 |
| EP | 0 337 035 | 11/1993 |
| EP | 0 646 365 | 4/1995 |
| WO | WO 83/03348 | 10/1983 |
| WO | WO 90/06723 | 6/1990 |
| WO | WO 95/33517 | 12/1995 |
| WO | WO 97/09926 | 3/1997 |
| WO | WO 97/32518 | 9/1997 |
| WO | WO 97/32519 | 9/1997 |
| WO | WO 97/33513 | 9/1997 |
| WO | WO99/34731 | 7/1999 |
| WO | WO 99/42176 | 8/1999 |
| WO | WO 99/62587 | 12/1999 |
| WO | WO 00/16686 | 3/2000 |
| WO | WO 01/00089 | 1/2001 |
| WO | WO01/87137 | 11/2001 |
| WO | WO01/97908 | 12/2001 |
| WO | WO 02/058551 | 8/2002 |
| WO | WO 03/061467 | 7/2003 |
| WO | WO03/061504 | 7/2003 |
| WO | WO 03/096889 | 11/2003 |

OTHER PUBLICATIONS

S.R. Vallanbhanei, J. Brennan, G. Gilling-Smith, D. Gould, T. How, R. McWilliams, P.L. Harris; Aortic Side Branch Perfusion Alone Does Not Account For High Intra-Sac Pressure After Endovascular Repair (EVAR) In The Absence Of Graft-Related Endoleak; Royal Liverpool University Hospital, Liverpool, UK.

M. Gawenda, J. Heckenkamp, M. Zaehringer, J. Brunkwall; "Intra-Aneurysm Sac Pressure—The Holy Gail Of Endoluminal Grafting of AAA"; Eur J Vasc Endovasc Surg, vol. 24, Aug. 2002, pp. 139-145.

G.W.H. Schurink, N.J.M. Arts, J.M Van Baalen, L.J. Schultze Kool, J.H. Van Bockel; "Experimental Study Of The Influence Of Endoleak Size On Pressure in The Aneurysm Sac And The Consequences Of Thrombosis"; British Journal of Surgery 2002, 87, pp. 71-78.

G.W.H. Schurink, N.J.M. Arts, J. Wild, J.M Van Baalen, T.A.M. Chuter, L.J. Schultze Kool, J.H. Van Bockel; "Endoleakage After Stent-Graft Treatment Of Abdominal Aneurysm: Implications On Presure And Imaging—An In Vitro Study"; Journal of Vascular Surgery, vol. 28, No. 2, pp. 234-241.

B. Sonesson, N. Dias, M. Malina, P. Olofsson, D. Griffin, B. Lindblad, K. Ivancev; "Intra-Aneurysm Pressure Measurements In Successfully Excluded Abdominal Aortic Aneurysm After Endovascular Repair"; Journal of Vascular Surgery, vol. 37, No. 4, Apr. 2003, pp. 733-738.

C.S. Skillern, S.L. Stevens, K. T. Piercy, R.L. Donnell, M. B. Freeman, M.H. Goldman; "Endotension In An Experiemental Aneurysm Model"; Journal of Vascular Surgery, vol. 36, No. 4, Oct. 2002, pp. 814-817.

G.D. Treharne, I.M. Loftus, M.M. Thompson, N. Lennard, J. Smith, G. Fishwick, P.R.F. Bell; "Quality Control During Endovascular Aneurysm Repair: Monitoring Aneurysmal Sac Pressure And Superficial Femoral Artery Flow Velocity": J. Endovasc Surg, 1999, 6, pp. 239-245.

M.L. Manwaring, V.D. Malbasa, K.L. Manwaring: "Remote Monitoring Of Intracranial Pressure"; Institute of Concology; Annals Of The Academy Of Studenica Apr. 2001; pp. 77-80.

K. Ouriel; "Role of Intrasac Pressure Measurements After EVAR: Can They Be Followed Noninvasively?"; Combined Session: Vascular Surgery and Interventional Radiology; VII 4.1.

R.A. Baum, J.P. Carpenter, C. Cope, M.A. Golden, O.C. Velazquez, D.G. Neschis, M.E. Mitchell, C.F. Barker, R.M. Fairman; "Aneurysm Sac Pressure Measurements After Endovascular Repair Of Abdominal Aortic Aneurysms"; Journal of Vascular Surgery, vol. 33, No. 1, Jan. 2001, pp. 32-41.

P.L. Harris, S. Dimitri; "Predicting Failure Of Endovascular Aneurysm Repair"; Eur J Vas Endovasc Surg. vol. 17, Jan. 1999; pp. 1-2.

G. Akingba, A. Cheng, A. Shum, P. Yang; "An Implantable Pressure Sensor For Aneurysmal Disease".

K.F. Adams, Jr.; "Guiding Heart Failure Care By Invasive Hemodynamic Measurements: Possible Or Useful?"; Journal of Cardiac Failure, vol. 8, No. 2, Apr. 2002, pp. 71-73.

A. Magalski, P. Adamson, F. Gadler, M. Boehm, D. Steinhaus, D. Reynolds, K. Vlach, C. Linde, B. Cremers, B. Sparks, T. Bennet; "Continuous Ambulatory Right Heart Pressure Measurements With An Implantable Hemodynamic Monitor: A Multicenter, 12-Month Follow-Up Study Of Patients With Chronic Heart Failure"; Journal of Cardiac Failure, vol. 8, No. 2, Apr. 2002, pp. 63-70.

R. Shabetai; "Monitoring Heart Failure Hemodynamics With An Implanted Device: Its Potential To Improve Outcome"; Journal of the American College of Cardiology; vol. 41, No. 4, Feb. 19, 2003; pp. 572-573.

J.C. Parodi, R. Berguer, L.M. Ferreira, R. Lamura, M.L. Schermerhorn; "Intra-eneurysmal Pressure After Incomplete Endovascular Exclusion"; Journal of Vascular Surgery, vol. 34, No. 5, Nov. 2001, pp. 909-914.

M. Gawenda, J. Heckenkamp, S. Winter, G. Jaschke, J. Brunkwall; "Pressure Is Transmitted Through PTFE And Dacron Grafts Leading To Aneurysm Sac Pressure Endoluminal Grafting of AAA—An In Vitro Study"; Vascular Centre, University of Cologne, Germany.

T. Akin, B. Ziaie, K. Najafi; "RF Telemetry Powering and Control of Hermetically Sealed Integrated Sensors and Actuators"; Center For Integrated Sensors and Circuits; Department of Electrical Engineering and Computer Science; University of Michigan; Ann Arbor, Michigan 48109-2122; pp. 145-148.

H.E. Haynes, A.L. Witchey; "Medical Electroncis: The Pill That Talks"; DEP, Camden, N.J.

A. DeHennis, K.D. Wise; "A Double-Sided Single-Chip Wireless Pressure Sensor"; Engineering Research Center For Wireless Integrated MicroSystems; Department of Electrical Engineering and Computer Science; The University of Michigan; Ann Arbor, Michigan 48109-2122.

J. Zhe, R.R. Farmer, V. Modi; "A MEMS Device For Measurement Of Skin Friction With Capacitive Sensing"; Department of Mechanical Engineering, Columbia University, New York, New York 10027; Microelectronics Research Center, New Jersey Institute of Technology, Newark, NJ 07102.

T. Chuter, K. Ivancev, M. Malina, T. Resch, J. Brunkwall, B. Lindblad, B. Risberg; "Endovascular And Surgical Techniques"; Eur J. Vasc Endovasc Surg vol. 13, Jan. 1997, pp. 85-87.

J.T. Farrar, C. Berkley, V.K. Zworykin; "Telemetering Of Intraenteric Pressure In Man By An Externally Energized Wireless Capsule"; Science, New Series, vol. 131, Issue 3416 (Jun. 17, 1960), 1814.

Collins, Miniature Passive Pressure Tansensor for Implanting in the Eye, IEEE Transactions on Bio-Medical Engineering, vol. BME-14, No. 2, Apr. 1967.

Sanchez et al., "Chronic Intraaneurysmal Pressure Measurements: An Experimental Method for Evaluating the Effectiveness of Endovascular Aortic Aneurism Exclusion", J. Vasc. Surg. vol. 26, No. 2, Aug. 1997.

Criado, et al., "An Aortic Aneurysm Model for the Evaluation of Endovascular Exclusion Prostheses", J. Vasc. Surg., vol. 22, No. 3, Sep. 1995.

* cited by examiner

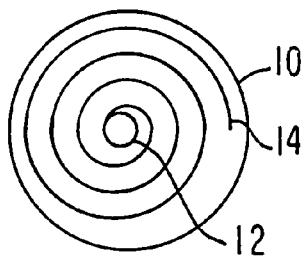 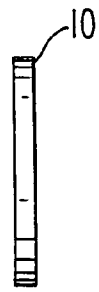 
FIG. 1          FIG. 2          FIG. 3
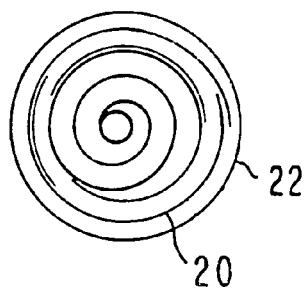 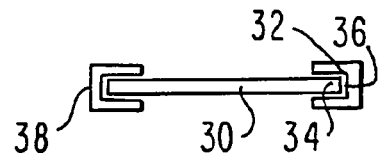
FIG. 4          FIG. 5

IMPLANTABLE WIRELESS SENSOR FOR PRESSURE MEASUREMENT WITHIN THE HEART

CROSS REFERENCE TO RELATED APPLICATION

This application is a continuation of co-pending, commonly assigned U.S. patent application Ser. No. 10/054,672, filed Jan. 22, 2002, now U.S. Pat. No. 6,855,115, issued Feb. 15, 2005, which is incorporated herein in its entirety.

FIELD OF THE INVENTION

This invention relates to chronically implanted sensors for wirelessly sensing pressure, temperature and other physical properties within the human body. More particularly, the invention concerns a wireless, un-powered micromachined pressure sensor that can be delivered using endovascular techniques to the interior of the human heart.

BACKGROUND OF THE INVENTION

The measurement of blood pressure within the human heart provides critical information regarding the organ's function. Many methods and techniques have been developed to give physicians with the ability to monitor heart function to properly diagnose and treat various diseases and medical conditions. For example, a sensor or transducer placed within the chambers of the heart can be used to record variations in blood pressure based on physical changes to a mechanical element within the sensor. This information is then transferred from the sensor to external device that is capable of translating the data from the sensor into a measurable value that can be displayed. The drawback of this type of sensor is that there must be a physical connection between the sensor and the external device, thus limiting its use to acute settings.

Many types of wireless sensors have been proposed that would allow implantation of the device into the body and then through the appropriate coupling means, pressure reading can be made over longer periods of interest. The primary limitation to these type of sensors are the fabrication methods used to manufacture them do not provide sufficient miniaturization to allow them to be introduced and implanted into the heart using non-surgical, catheter based techniques.

For a sensor that is designated to be placed within the heart, additional considerations are required. A feature must be provided that will allow the sensor to be permanently secured to the wall of the heart in a manner that will exclude any possibility of movement of the sensor or displacement out of the heart. Finally, an implantable sensor of this type must be assembled using the materials and fabrications methods that ensure appropriate biocompatibility and long term mechanical and electrical durability.

One method of manufacturing a sensor capable of measuring pressure is to use a capacitor that is assembled such that the capacitive plates will deform as a result of exposure externally applied stress. This deformation will result in a change in the capacitance that will be proportional to the applied stress. Various patents describe the fabrication and use of capacitor based pressure sensors. The primary limitation of many of these inventions is that the techniques used to fabricate the sensors do not lend themselves to miniaturization necessary for it to be configured as an implantable medical device.

The fabrications methodologies that have been developed in the field of Micro-Electro-Mechanical Systems, however, do specifically provide the means for assembling miniaturized sensors capable of measuring a variety of properties including pressure. MEMS devices as described in these patents traditionally use silicon as a substrate for construction of miniature electrical or mechanical structures. The resulting sensors are inherently rigid severely limiting the ability to manipulate them into temporarily small packages that would provide the means for non-surgical implantation into the human body.

A number of patents detail pressure sensors (some capacitive in nature, some manufactured using MEMS based technology) that are specifically designed for implantation into the human body. These sensors suffer from many of the limitations already mentioned with the additional concerns that they require either the addition of a power source to operate the device or the need for a physical connection to a device capable of translating the sensor output into a meaningful display of a physiologic parameter.

To overcome these two problems (power and physical connection), the concept of a externally modulated LC circuit has been applied to development of implantable pressure sensors. Of a number of patents that describe a sensor design of this nature, Chubbuck, U.S. Pat. No. 6,113,553 is a representative example. The Chubbuck patent demonstrates how a combination of a pressure sensitive capacitor placed in series with an inductor coil provides the basis of a wireless, un-powered pressure sensor that is suitable for implantation into the human body. Construction of an LC circuit in which variations of resonant frequency correlate to changes in measured pressure and which these variations can be detected remotely through the use of electromagnetic coupling are further described in Allen et al., U.S. Pat. No. 6,111,520, incorporated herein by reference.

The device embodied by the Chubbuck patent is manufactured using conventional techniques, thus requiring surgical implantation and thus limiting its applicability to areas that are easily accessible to surgery (i.e., skull).

Thus, the need exists for a biocompatible, wireless, unpowered pressure sensor that for the purposes of introduction and delivery within the human heart can be manipulated into a smaller shape and size by rolling or folding it into a cylindrical form and loaded into a small diameter catheter. Then upon positioning the catheter within the desired chamber of the heart, the sensor can be deployed and through the use super-elastic alloy components in the form of anchors or hooks secured to the interior wall of the heart.

OBJECTS OF THE INVENTION

It is an object of this invention to provide an implantable wireless sensor.

It is also an object of this invention to provide a wireless, unpowered micromechanical, flexible sensor that can be delivered endovascularly to a heart chamber.

It is a further object of this invention to provide an implantable, wireless, unpowered sensor that can be delivered endovascularly to a heat chamber to measure pressure and/or temperature.

These and other objects of the invention will become more apparent from the discussion below.

SUMMARY OF THE INVENTION

The present invention describes a sensor that can be fabricated using micro-machining techniques and can be implanted into the human body using non-surgical methods for the measurement of physical parameters. This sensor is fabricated using MicroElectroMechanical Systems (MEMS) technology, which allows the creation of a flexible device that is small, accurate, precise, durable, robust, biocompatible, radiopaque and insensitive to changes in body chemistry, biology or external pressure. This device will not require the use of wires to relay pressure information externally nor need an internal power supply to perform its function.

The MEMS approach to sensor design lends itself to the fabrication of small, flat sensors that can be formed using biocompatible polymers as substrate materials. The pressure sensor described above can then be manipulated into a smaller shape and size by rolling, bending, or folding it into a cylindrical form. This smaller object can then be introduced into the chambers of the human heart using endovascular catheter techniques. Once positioned within the heart, the device unfurls into a preferred flat shape. Super-elastic alloy components may be incorporated into the device such as hooks, anchors, harpoons or coils are designed to secure the pressure sensor to the wall of the heart and resist displacement due to movement of the heart wall or from the interaction of blood being pumped through the heart. In addition, appropriately biocompatible coatings may be applied to the surface of the sensor in order to prevent adhesion of biological substances to the sensor that could interfere with it proper function.

The pressure sensor can be manufactured using Micromachining techniques that were developed for the integrated circuit industry. An example of this type of sensor features an inductive-capacitive (LC) resonant circuit with a variable capacitor and is described in Allen et al., U.S. Pat. No. 6,111,520 incorporated herein by reference. In this sensor, the capacitance varies with the pressure of the environment in which the capacitor is placed. Consequently, the resonant frequency of the LC circuit of the pressure sensor varies depending on the pressure of the environment. The pressure sensor is made of completely passive components having no active circuitry or power sources such as batteries. The pressure sensor is completely self-contained having no leads to connect to an external circuit or power source. Furthermore, these same manufacturing techniques can be used to add additional sensing capabilities, such as the ability to measure temperature by the addition of a resistor to the basic LC circuit.

When introduced into heart, the pressure sensor can provide pressure related data by use of an external measuring device. As disclosed in the Allen et al. patent, several different excitation systems can be used. For example, the sensor can be electromagnetically coupled to a transmitting antenna. Consequently, a current is induced in the sensors, which oscillates at the resonant frequency of the sensor. This oscillation causes a change in the frequency spectrum of the transmitted signal. From this change, the bandwidth and resonant frequency of the particular sensor may be determined, from which the corresponding change in pressure can be calculated.

Accordingly, the present invention provides for an impedance system and method of determining the resonant frequency and bandwidth of a resonant circuit within a particular sensor. The system includes a transmitting antenna, which is coupled to an impedance analyzer. The impedance analyzer applies a constant voltage signal to the transmitting antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from transmitting antenna, and, electromagnetically coupling a resonant circuit on a sensor to the transmitting antenna thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies is applied to the transmitting antenna for a predetermined period of time, thereby inducing a current in the resonant circuit of the sensor at the resonant frequency. The system then listens for a return signal which radiates from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna thereby inducing a current in the sensor circuit, listening for and receiving a return signal radiated from the sensor circuit, and determining the resonant frequency and bandwidth from the return signal.

In addition, the present invention provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The above methods lend themselves to the creation of small and simple to manufacture hand-held electronic devices that can be used without complication.

Other features and advantages of the present invention will become apparent to one with skill in the art upon examination of the following drawings and detailed description. It is intended that all such additional features and advantages be included herein within the scope of the present invention, as defined by the claims.

Thus, this patent discloses a simple method of monitoring the pressure within the human heart by inserting a pressure transducer using a catheter and using a small, hand-held read device to measure the pressure easily, safely, inexpensively and accurately. It also includes a method of introducing the sensor into the body by using the steps of folding or rolling the sensor into a cylinder, loading it into a catheter and deploying into the heart by allowing it to unroll or unfold, either by itself or facilitated by the incorporation of a super-elastic alloy component. The same super-elastic element also provides the means to permanently securing the device to the interior of the heart.

Delivery of the device of the invention to a heart chamber may be accomplished as follows: Using the standard Seldinger technique, the physician gains access to the patient's jugular artery and places a vessel introducer with a hemostatic valve. Under direct fluoroscopic visualization, a flexible guidewire is inserted through the introducer catheter and maneuvered such that its tip is stationed within a chamber of the heart. In a preferred delivery system a catheter has a "daisy shape" sensor folded into its distal end, so that the middle, flat section of the sensor is essentially normal to the longitudinal axis of the catheter. A solid or hollow cylindrical rod or member is pushed distally to push the sensor from the distal end of the catheter and, optionally, to attach to an inner wall of the heart chamber with an anchor member.

Optionally, a coaxial delivery catheter consisting of two hollow extruded polymeric catheters, the smaller of the two disposed inside the larger one, is inserted over the guidewire and through the introducer and advanced distally until its tip is within the heart chamber. The smaller catheter has an annular space to hold a folded sensor, which is released when the outer catheter is withdrawn proximally.

In a preferred delivery procedure, a sensor is attached to a small diameter, proximally extending "safety" or tether wire. The sensor and safety wire are also positioned in a lumen in a catheter or in the annular space between two coaxial catheters, but the safety wire runs the entire length of the delivery catheter and extends proximally past the proximal end of that catheter outside the patient. In this configuration, the sensor remains secured to the tether wire after the coaxial delivery catheter is removed from the patient. The sensor is detached from the tether wire using any of the methods known in the art, and the wire is removed.

In a further alternative delivery procedure the sensor can be loaded into the annular space between the inner and outer catheters by inserting the sensor into a longitudinal slit cut into the outer catheter and attaching a tab on the sensor's surface into a slot cut into the inner coaxial catheter. By rotation of the inner tube, the sensor will be retracted through the slit and positioned in the annular space between the two tubes. To deploy the device, the rotation of the inner tube is reversed and the sensor emerges through the slit of the outer catheter. There are two specific advantages to this deployment mechanism. First, the sensor can be packaged and stored in a flat configuration. This is desirable since long term storage in a pre-loaded curved geometry could make it more difficult for the sensor to re-establish the flat arrangement that is optimal for effective electromagnetic inductive coupling with the external read-out unit. The second advantage is that by cutting the longitudinal slit at angle that is offset from the main axis of the outer tube, the sensor will be biased into a planar configuration as it is forced through the slit during the deployment process.

A safety wire system can also be used with this mechanism, although the wire may be external to the outer coaxial tube. As described above, the wire will remain attached to the sensor during the deployment process and will stay within the heart chamber while the delivery catheter is removed. Subsequent to insertion and deployment of the stent-graft, the wire will be detached from the sensor and pulled out of the body.

The detachment of the wire from the sensor can be accomplished in several ways. The wire may be simply glued to the sensor using an adhesive. To separate the sensor from the wire, a thin-walled, metal or polymer tube is passed along the length of the wire and positioned at the adhesive joint. While holding this tube steady, the wire is then retracted into the tube. Sufficient traction can be applied to the segment of the wire that remains outside of the body to cause the adhesive to joint to fail and allow removal of the wire.

An alternative method would rely on a mechanical connection between the wire and sensor such as adding threads to the end of the wire which could then be connected to a matching threaded female receptacle on the sensor. To separate the wire from the sensor, counter-rotation would be applied to the wire until the threads disengage. One could envision many variations of this design that would involve the mechanical locking and un-locking of two mating components.

BRIEF DESCRIPTION OF THE DRAWINGS

FIG. 1 is a front view of an embodiment of the invention;

FIG. 2 is a lateral view of the embodiment of the invention shown in FIG. 1;

FIG. 3 is a lateral view of an embodiment of the invention of FIG. 1 folded for delivery;

FIG. 4 is a front view of another embodiment of the invention;

FIG. 5 is a lateral view of a yet further embodiment of the invention;

DETAILED DESCRIPTION OF THE INVENTION

Figure 6:
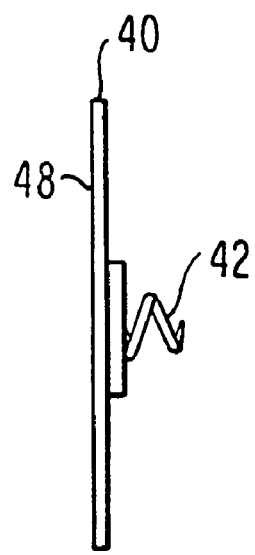
FIGS. 6 and 7 are each a lateral view of an embodiment of the invention with an anchoring mechanism.

The invention can perhaps be better understood by referring to the drawings. One embodiment of a sensor according to the invention is shown in FIGS. 1, 2, and 3, where a disc-shaped sensor 10 comprises a capacitor disk 12 and a wire spiral 14. FIG. 2 is a lateral view of sensor 10, and FIG. 3 is a lateral view of sensor 10 in a folded configuration for insertion. The fact that sensor 10 is sufficiently flexible to be folded as shown in FIG. 4 is an important aspect of the invention.

In FIG. 4 a ring 20 comprised of a shape memory alloy such as nitinol has been attached to, for example, with adhesive, or incorporated into, for example, layered within, a sensor 22.

FIG. 5 is a lateral cross-sectional view of a circular sensor 30 having a ring 32 comprised of a shape memory alloy such as nitinol encompassing the outer edge 34 of sensor 30. Ring 32 preferably is attached to outer edge 34 by a suitable physiologically acceptable adhesive 36, such as an appropriate epoxy or cyanoacrylate material. Preferably the ring will be radiopaque.

The size of the circular sensors of the invention will vary according to factors such as the intended application, the delivery system, etc. The circular sensors are intended to be from about 0.5 to about 3 cm in diameter, with a thickness of from about 0.05 to about 0.30 in. When a ring 32 is employed, the thickness of the ring, i.e., the width of the outside surface 38, will preferably be from about 1.5 to about 3.5 times the thickness of the sensor.

Figure 7:
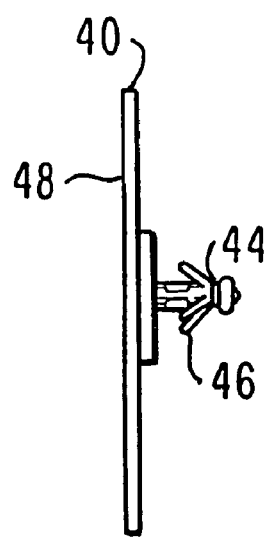

FIGS. 6 and 7 each represent a lateral view of a sensor with an anchoring member. In FIG. 6 sensor 40 has a screw/coil 42, and in FIG. 7 sensor 40 has an anchor 44 with umbrella-like projections 46. When pressure is applied to the flat side 48 of sensor 40, anchor 42 or 44 will penetrate a vessel wall, organ wall, or other substrate to cause sensor 36 to remain in a desired position or location. Alternatively, an anchoring mechanism such as is shown in FIGS. 6 and 7 could be attached to ring 32 in FIG. 5.

The pressure sensor of the invention can be manufactured using Micro-machining techniques that were developed for the integrated circuit industry. An example of this type of sensor features an inductive-capacitive (LC) resonant circuit with a variable capacitor, as is described in Allen et al., U.S. Pat. No. 6,111,520, all of which is incorporated herein by reference. The sensor contains two types of passive electrical components, namely, an inductor and a capacitor. The sensor is constructed so that the fluid pressure at the sensor's surface changes the distance between the capacitor's parallel plates and causes a variation of the sensor's capacitance.

Figure 8:
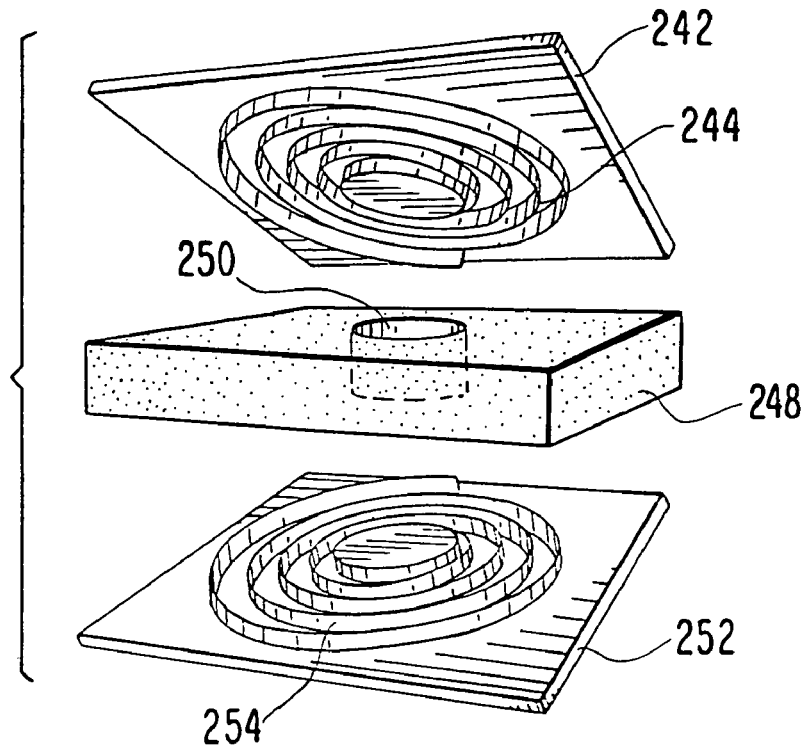
FIG. 8 is an exploded schematic representation of construction of one embodiment of a sensor.

In a preferred embodiment the sensor of the invention is constructed by laminating several layers of material together, as shown, for example, in FIG. 8. A first layer 242 is fabricated from a sheet of polyimide film (e.g. KAPTON, available from Du Pont) upon which a micro-machined copper pattern 244 is deposited. Pattern 244 preferably consists of a circular conductive segment in the center of the sheet surrounded by a spiral coil. A second layer 248 comprises a sheet of flexible adhesive through which hole 250 has been cut in the center. (Optionally there may be more than one such layer 248.) A final layer 252 is another sheet of polyimide film with a copper pattern 254 that is a mirror image of pattern 244. When assembled, the first, second, and third layers are aligned such that the holes in the middle adhesive layers are centered between the circular conductive segments in the middle of the two outer polyimide layers 242 and 252. In this way a capacitor (defined as an electric circuit element used to store charge temporarily, consisting in general of two metallic plates separated and insulated from each other by a dielectric) is formed. At the same time, the two metal spirals on the polyimide sheets 242 and 252 form an inductor component of a miniature electrical circuit.

The sensor exhibits the electrical characteristics associated with a standard LC circuit. An LC circuit is simply a closed loop with only two elements, a capacitor and an inductor. If a current is induced in the LC loop, the energy in the circuit is shared back and forth between the inductor and capacitor. The result is an energy oscillation that will vary at a specific frequency. This is termed the resonant frequency of the circuit and it can be easily calculated as its value is dependent on the circuit's inductance and capacitance. Therefore, a change in capacitance will cause the frequency to shift higher or lower in linear proportion to the change in the value of capacitance.

As noted above, the capacitor in the assembled pressure sensor consists of the two circular conductive segments separated by an air gap. If a pressure force is exerted on these segments it will act to deform the outer polyimide sheet and move the two conductive segments closer together. This will have the effect of reducing the air gap between them which will consequently change the capacitance of the circuit. The result will be a shift in the circuit's resonant frequency that will be in direct proportion to the force applied to the sensor's surface.

Because of the presence of the inductor, it is possible to electromagnetically couple to the sensor and induce a current in the circuit. This allows for wireless communication with the sensor and the ability to operate it without the need for an internal source of energy such as a battery. Thus, if the sensor is located within the chamber of the heart, it will be possible to determine the pressure within the chamber in a simple, non-invasive procedure by remotely interrogating the sensor, recording the resonant frequency and converting this value to a pressure measurement. The readout device generates electromagnetic energy that penetrates through the body's tissues to the sensor's implanted location. The sensor's electrical components absorb a fraction of the electromagnetic energy that is generated by the readout device via inductive coupling. This coupling induces a current in the sensor's circuit oscillates at the same frequency as the applied electromagnetic energy. Due to the nature of the sensor's electromechanical system there exists a frequency of alternating current at which the absorption of energy from the readout device is at a minimum. This frequency is a function of the capacitance of the device. Therefore, if the sensor's capacitance changes, so will the frequency at which it minimally absorbs energy from the readout device. Since the sensor's capacitance is mechanically linked to the fluid pressure at the sensor's surface, a measurement of this frequency by the readout device gives a relative measurement of the fluid pressure. If calibration of the device is performed, then an absolute measurement of pressure can be made. See, for example, the extensive discussion in the Allen et al. patent, again incorporated herein by reference, as well as Gershenfeld et al., U.S. Pat. No. 6,025,725, incorporated herein by reference.

The pressure sensor is made of completely passive components having no active circuitry or power sources such as batteries. The pressure sensor is completely self-contained having no leads to connect to an external circuit or power source. Furthermore, these same manufacturing techniques can be used to add additional sensing capabilities, such as the ability to measure temperature by the addition of a resistor to the basic LC circuit.

Figure 9:
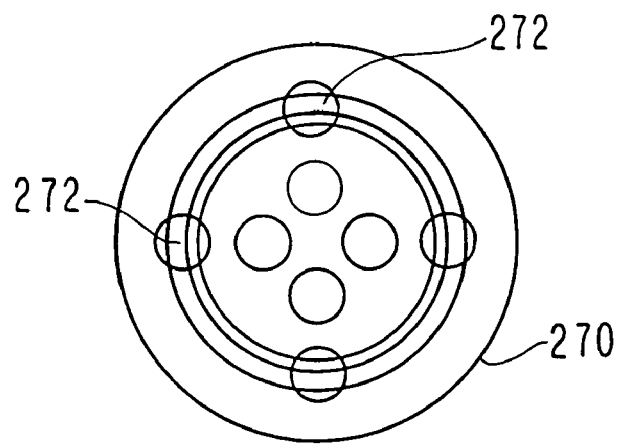
FIG. 9 is a schematic representation of an embodiment of the invention with distributed capacitance.

Several alternative configurations of the LC circuit design can be considered to address specific biological and manufacturing issues. For example, in one embodiment of the sensor the capacitor element consists of two plates that are separated by a suitable dielectric material, such as air, inert gas, fluid or a vacuum. To ensure the long term integrity of the sensor, various coatings could be applied to the surface or between the polymeric layers used to form the sensor. These coating can be used to provide a hermetic seal that will prevent leakage of body fluids into the cavity or permeation of the cavity material (gas, vacuum or fluid) out of the sensor. In an another embodiment of the invention, shown in FIG. 9, a sensor 270 has a multitude of capacitors 272 formed either as separate elements or as an array. In such a distributed capacitance configuration, there can be a more accurate and more sensitive measurement of pressure.

It is within the scope of the invention that the frequency response to the sensor will be in the range of from about 1 to about 200 $MH_z$, preferably from about 1 to about 100 $MH_z$, and more preferably from about 2 to about 90 $MH_z$, with a Q factor from about 5 to about 80, preferably from about 10 to about 70, more preferably from about 10 to 60.

In a further embodiment of the invention there is no direct electrical connection between the two sides of the LC circuit. Referring again to the sensor described in the Allen et al. patent, the device is constructed using multiple layers upon lie the necessary circuit elements. Disposed on the top and bottom layer are metal patterns constructed using micromachining techniques which define a top and bottom conductor and a spiral inductor coil. To provide for an electrical contact between the top and bottom layers small vias or holes are cut through the middle layers. When the layers are assembled, a metal paste is forced into the small vias to create direct electrical connections or conduits. However, experimentation has shown that due to parasitic capacitance that is created between the top and bottom inductor coils, a vialess operational LC circuit can be created. This absence of via holes represents a significant improvement to the sensor in that it simplifies the manufacturing process and, more importantly, significantly increases the durability of the sensor making it more appropriate for use inside the human body.

Figure 10:
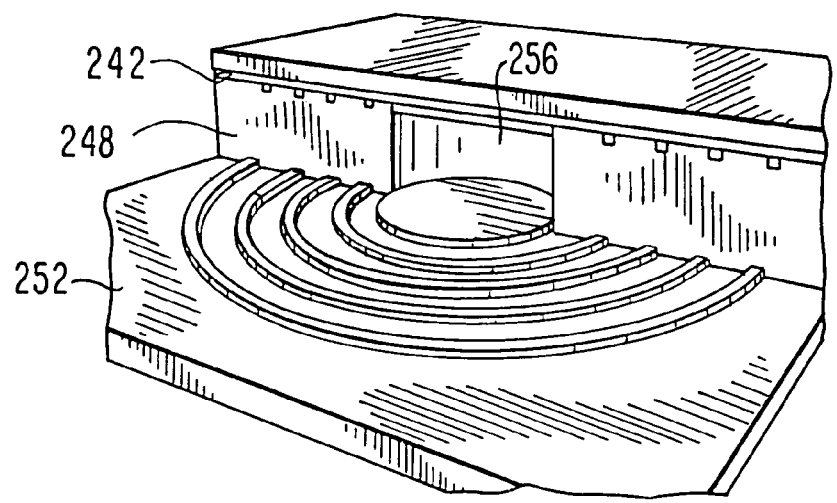
FIGS. 10 and 11 are each a schematic, partial cross-sectional view of an embodiment of a sensor according to the invention.
Figure 11:
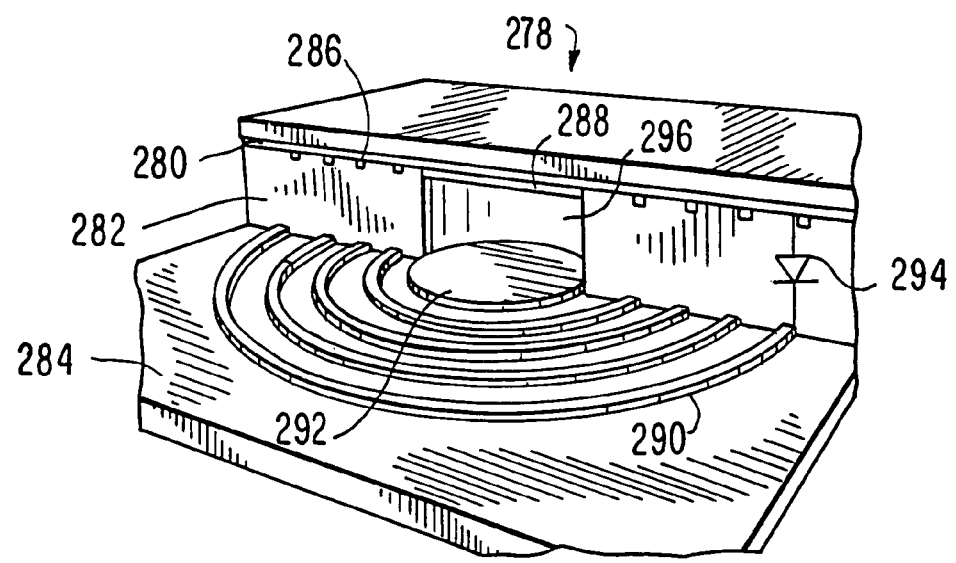

FIG. 10 is a partial cross-sectional review of the sensor shown in FIG. 8, where first layer 242, second layer 248, and third layer 252 are sandwiched together. A cylindrical space 256 comprises a pressure sensitive capacitor. No via holes are present. The sensor 278 shown in FIG. 11 comprises a first polyimide layer 280, a second, adhesive layer 282, and a third, polyimide layer 284. First layer 280 has a copper pattern comprising a coil 286 and a disk 288, and third layer 284 comprises a coil 290 and a disk 292. A cylindrical space 296 comprises a pressure sensitive capacitor. A diode 294 connected between coils 286 and 290 creates a non-linear sensor, i.e., a sensor where the frequency change is non-linear as compared to a change in pressure.

The design of the sensor is not limited to a specific geometric configuration. In the specific example noted above the inductor component is described as a spiral coil. Other embodiments of the sensor could utilize oval, rectangular or an amorphous shape. Specific electrical, mechanical and biologic advantages could be obtained by employing these various geometric designs. By way of example, a rectangular shaped sensor in which the ratio of length to width was greater than four would greater lend itself to catheter based delivery as is would minimize the radius of curvature required to position the folded device within a small diameter catheter. Alternatively, a more elaborate shape, such as one resembling the petals of a flower, would lend itself to more complex folding patterns that could facilitate delivery to specific areas of a chamber of the heart.

Figure 12:
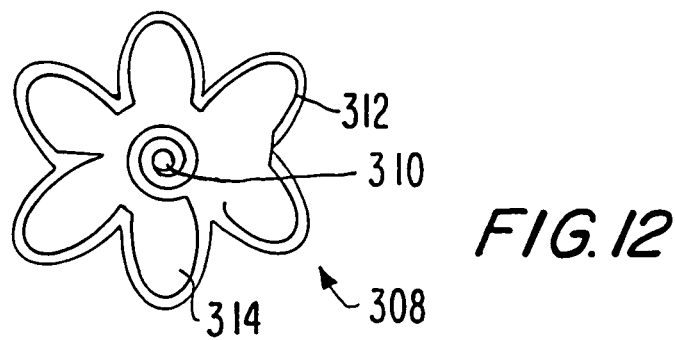
FIG. 12 is a schematic representation of an alternate shape for an embodiment of the invention.
Figure 13:
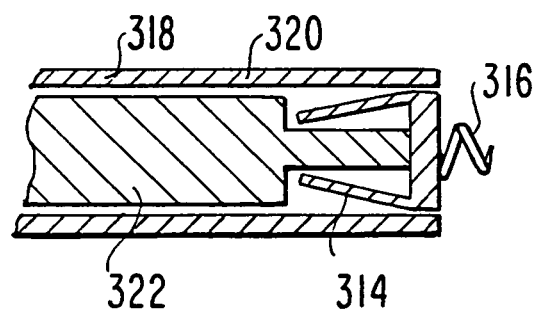
FIG. 13 is a cross-sectional view of the distal end of a delivery catheter with the embodiment shown in FIG. 12.

In a preferred embodiment of the invention a foldable sensor is delivered to the chamber of a patient's heart in the distal end of a delivery catheter. The sensor can be regularly or irregularly shaped so that outer portions of the sensor can fold to about a 90° angle as compared to a relatively flat, middle portion of the sensor. For example, in FIG. 12, a daisy or flower-shaped sensor 308 has a capacitor surface 310 connected to a wire 312 that partly follows the outer configuration of sensor 308. Petals 314 fold so that sensor 308 with a distal anchor 316 can be "loaded" into a catheter 318, as shown in FIG. 13. When the distal end 320 of catheter 318 is in position, a pushing rod member 322 is pushed distally to cause sensor 308 to be released from catheter 318 and attach to the inner surface of the wall of a heart chamber (not shown).

It is especially preferred that rod member 322 will be temporarily affixed to sensor 308 for at least two purposes. First, rod member 322 functions as a safety or tether wire. And second, rod member 322 will be capable of twisting or otherwise maneuvering sensor 308 so that anchor 368 will attach to the heart chamber wall. Once sensor 308 is attached, rod member 322 is disengaged from sensor 308 and withdrawn proximally.

Figure 14:
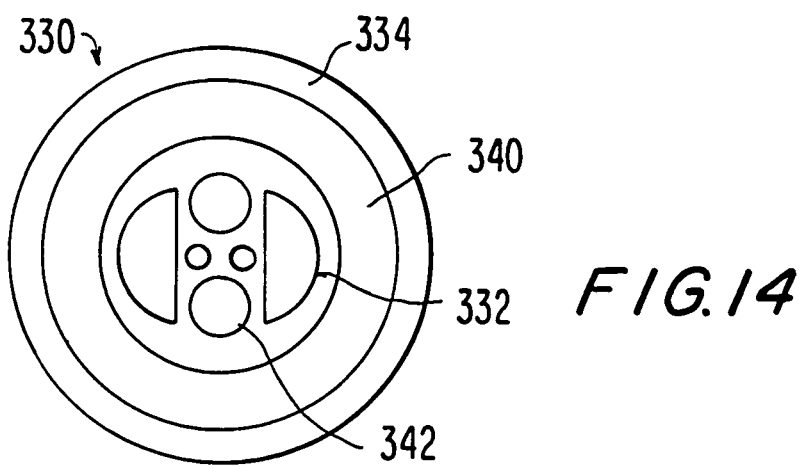
FIG. 14 is a schematic of another sensor according to the invention.

Another, embodiment of a sensor is shown in FIG. 14, where circular sensor 330 comprises flexible cut-outs 332. The first outer layer 334 comprises a polymide substrate with a copper pattern comprising a coil 340 and several, from 2 to 6, disks 342 to form pressure sensitive capacitors. Sensor 330 also comprises at least one adhesive layer (not shown) and a third outer layer corresponding to the first outer layer (not shown). Preferably sensor 330 has at least one diode connecting the copper coils of the first and third layers.

The flexible cut-outs 352 facilitate, among other things, folding of sections of sensor 370 for placement in, or arrangement upon, a delivery catheter, such as in FIG. 13. The sections can also be folded to create either a "Z" shape or, for example, a "U" shape, for other applications. It is within the scope of the invention that variously numbered and shaped cut-outs could be used for particular applications.

While a preferred delivery system is described above, it is within the scope of the invention that other delivery systems could be employed. Other such delivery systems are described in, for example, co- pending, commonly assigned U.S. patent application Ser. No. 10/054,672, filed Jan. 22, 2002, now U.S. Pat. No. 6,855,115, issued Feb. 15, 2005, incorporated herein by reference.

Further, the invention is not limited to the implantation of a single sensor. Since the biological environment within a patient's heart is not necessarily homogeneous, multiple pressure sensors may be introduced into a patient's heart, each being positioned at different locations. In this situation, each sensor may be designed with a unique signature (obtained by changing the resonant frequency of the sensor), so that the pressure measurement derived from one sensor can be localized to its specific position within the heart.

Figure 15:
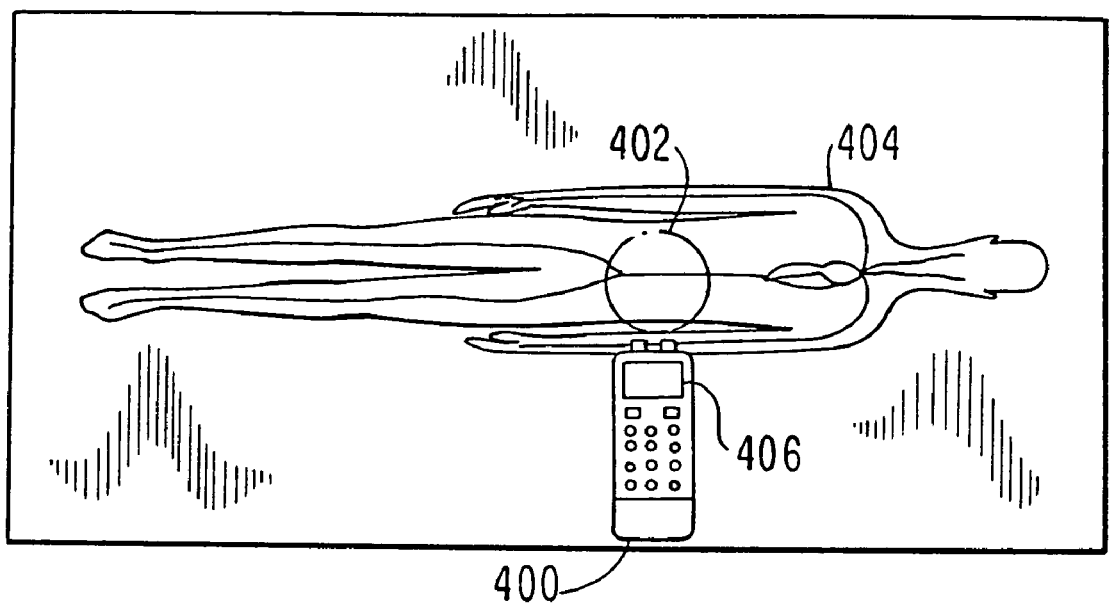
FIG. 15 is a drawing of a read-out device employed according to the invention.

When introduced into the chamber of a patient's heart, the pressure sensor can provide pressure related data by use of an external measuring device. As disclosed in the Allen et al. patent, several different excitation systems can be used. The readout device generates electromagnetic energy that can penetrate through the body's tissues to the sensor's implanted location. The sensor's electrical components can absorb a fraction of the electromagnetic energy that is generated by the readout device via inductive coupling. This coupling will induce a current in the sensor's circuit that will oscillate at the same frequency as the applied electromagnetic energy. Due to the nature of the sensor's electromechanical system there will exist a frequency of alternating current at which the absorption of energy from the readout device is at a minimum. This frequency is a function of the capacitance of the device. Therefore, if the sensor's capacitance changes so will the frequency at which it minimally absorbs energy from the readout device. Since the sensor's capacitance is mechanically linked to the fluid pressure at the sensor's surface, a measurement of this frequency by the readout device can give a relative measurement of the fluid pressure. If calibration of the device is performed then an absolute measurement of pressure can be made The circuitry used to measure and display pressure is contained within a simple to operate, battery powered, hand-held electronic unit 400, as shown in FIG. 15. This unit 400 also contains the antenna 402 needed to perform the electromagnetic coupling to the sensor. The antenna may be integrated into the housing for the electronics or it may be detachable from the unit so that it can be positioned on the surface of the body 404 in proximity to the implanted sensor and easily moved to optimize the coupling between antenna and sensor. The antenna itself may consist of a simple standard coil configuration or my incorporate ferrous elements to maximize the coupling efficiency. The electronic device would feature an LCD or LED display 406 designed to clearly display the recorded pressure in physiologically relevant units such as mm HG. In an alternative embodiment, the display may be created by integrating a commercially available hand-held computing device such as a Palm® or micro-PC into the electronic circuitry and using this device's display unit as the visual interface between the equipment and its operator. A further advantage of this approach is that the hand-held computer could be detached from the read-out unit and linked to a standard desktop computer. The information from the device could thus be downloaded into any of several commercially available data acquisition software programs for more detailed analysis or for electronic transfer via hard media or the internet to a remote location.

Accordingly, the present invention provides for an impedance system and method of determining the resonant frequency and bandwidth of a resonant circuit within a particular sensor. The system includes a transmitting antenna, which is coupled to an impedance analyzer. The impedance analyzer applies a constant voltage signal to the transmitting antenna scanning the frequency across a predetermined spectrum. The current passing through the transmitting antenna experiences a peak at the resonant frequency of the sensor. The resonant frequency and bandwidth are thus determined from this peak in the current.

The method of determining the resonant frequency and bandwidth using an impedance approach may include the steps of transmitting an excitation signal using a transmitting antenna and electromagnetically coupling a sensor having a resonant circuit to the transmitting antenna thereby modifying the impedance of the transmitting antenna. Next, the step of measuring the change in impedance of the transmitting antenna is performed, and finally, the resonant frequency and bandwidth of the sensor circuit are determined.

In addition, the present invention provides for a transmit and receive system and method for determining the resonant frequency and bandwidth of a resonant circuit within a particular sensor. According to this method, an excitation signal of white noise or predetermined multiple frequencies is transmitted from a transmitting antenna, the sensor being electromagnetically coupled to the transmitting antenna. A current is induced in the resonant circuit of the sensor as it absorbs energy from the transmitted excitation signal, the current oscillating at the resonant frequency of the resonant circuit. A receiving antenna, also electromagnetically coupled to the transmitting antenna, receives the excitation signal minus the energy which was absorbed by the sensor. Thus, the power of the received signal experiences a dip or notch at the resonant frequency of the sensor. The resonant frequency and bandwidth are determined from this notch in the power.

The transmit and receive method of determining the resonant frequency and bandwidth of a sensor circuit includes the steps of transmitting a multiple frequency signal from transmitting antenna, and, electromagnetically coupling a resonant circuit on a sensor to the transmitting antenna thereby inducing a current in the sensor circuit. Next, the step of receiving a modified transmitted signal due to the induction of current in the sensor circuit is performed. Finally, the step of determining the resonant frequency and bandwidth from the received signal is executed.

Yet another system and method for determining the resonant frequency and bandwidth of a resonant circuit within a particular sensor includes a chirp interrogation system. This system provides for a transmitting antenna which is electromagnetically coupled to the resonant circuit of the sensor. An excitation signal of white noise or predetermined multiple frequencies is applied to the transmitting antenna for a predetermined period of time, thereby inducing a current in the resonant circuit of the sensor at the resonant frequency. The system then listens for a return signal which radiates from the sensor. The resonant frequency and bandwidth of the resonant circuit are determined from the return signal.

The chirp interrogation method for determining the resonant frequency and bandwidth of a resonant circuit within a particular sensor includes the steps of transmitting a multi-frequency signal pulse from a transmitting antenna, electromagnetically coupling a resonant circuit on a sensor to the transmitting antenna thereby inducing a current in the sensor circuit, listening for and receiving a return signal radiated from the sensor circuit, and determining the resonant frequency and bandwidth from the return signal.

Figure 16:
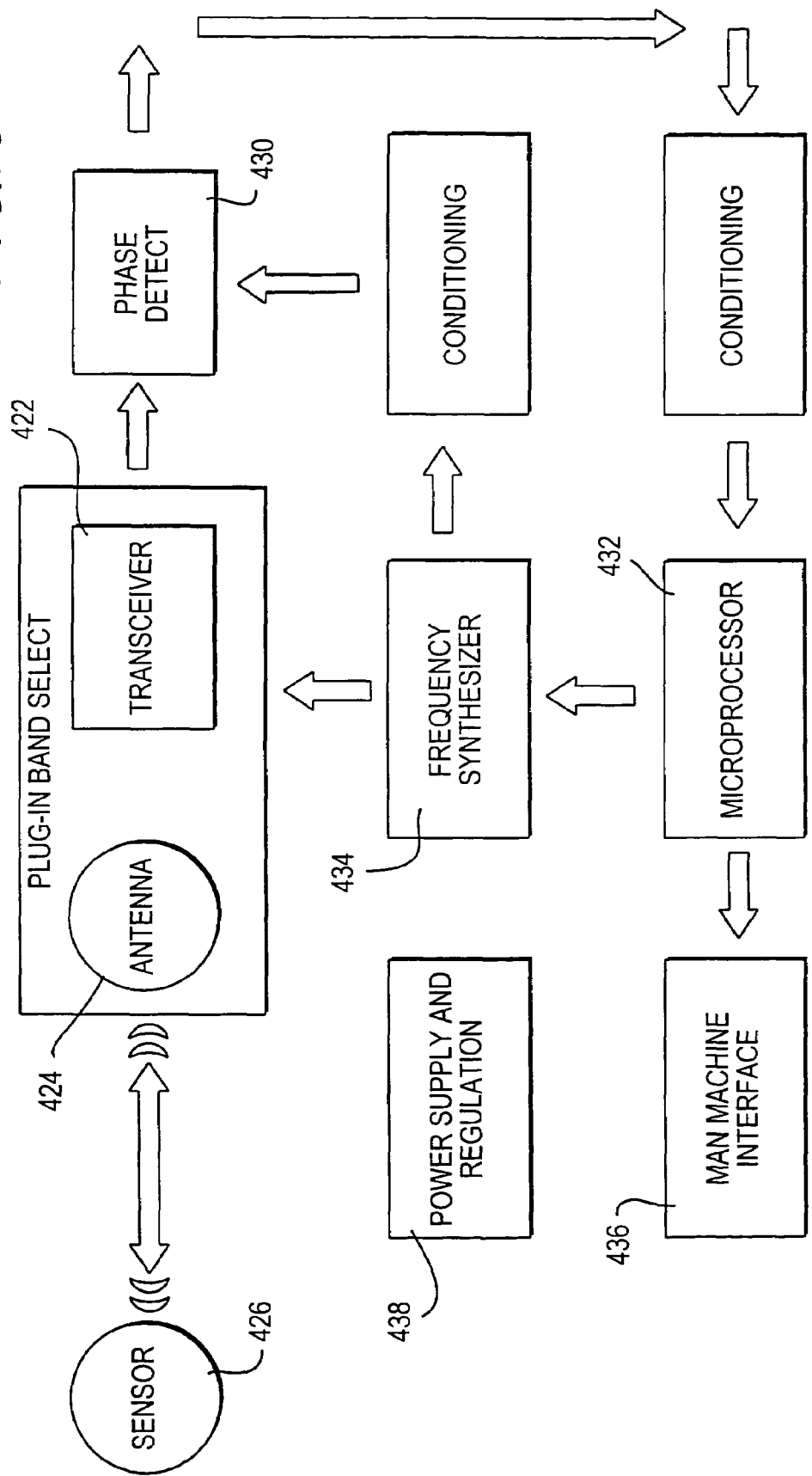
FIG. 16 is a block diagram of an electrical circuit useful according to the invention.

A representative block diagram of an electrical circuit that can be used to interrogate the sensor and determine the resonant frequency is shown in FIG. 16. A transmitter and receiver, i.e., a transceiver 422, has an antenna 424 for generating and receiving signals from a sensor 426. Transceiver 422 is an electronic or digital connection with a phase detector 430, a microprocessor 432, and a frequency synthesizer 434. Microprocessor 432 is in turn connected to an interface 436 such as a terminal. Power supply 438 regulates and provides electrical power to the system.

The present invention also provides an analog system and method for determining the resonant frequency of a resonant circuit within a particular sensor. The analog system comprises a transmitting antenna coupled as part of a tank circuit which in turn is coupled to an oscillator. A signal is generated which oscillates at a frequency determined by the electrical characteristics of the tank circuit. The frequency of this signal is further modified by the electromagnetic coupling of the resonant circuit of a sensor. This signal is applied to a frequency discriminator which in turn provides a signal from which the resonant frequency of the sensor circuit is determined.

The analog method for determining the resonant frequency and bandwidth of a resonant circuit within a particular sensor includes the steps of generating a transmission signal using a tank circuit which includes a transmitting antenna, modifying the frequency of the transmission signal by electromagnetically coupling the resonant circuit of a sensor to the transmitting antenna, and converting the modified transmission signal into a standard signal for further application.

The invention further includes an alternative method of measuring pressure in which a non-linear element such as a diode or polyvinylidenedifloride piezo-electric polymer is added to the LC circuit. A diode with a low turn-on voltage such as a Schottky diode can be fabricated using micromachining techniques. The presence of this non-linear element in various configurations within the LC circuit can be used to modulate the incoming signal from the receiving device and produce different harmonics of the original signal. The read-out circuitry can be tuned to receive the particular harmonic frequency that is produced and use this signal to reconstruct the fundamental frequency of the sensor. The advantage of this approach is two-fold; the incoming signal can be transmitted continuously and since the return signal will be at different signals, the return signal can also be received continuously.

The above methods lend themselves to the creation of small and simple to manufacture hand-held electronic devices that can be used without complication.

One additional concern regarding devices designated for long term implantation in the human body is maintenance of electrical stability over time as the environment the sensor has been placed in changes. Under this scenario the sensor's accuracy may drift from its original baseline. It would thus be desirable to have available to the user of the device, a method for determining if the sensor is functioning properly and also to be able to recalibrate the device anytime after it has been implanted. This invention therefore also includes a method of using acoustic energy to challenge the sensor and determining to what degree (if any) sensor performance has been degraded. In this method, energy in the ultrasound range is directed towards the sensor and a measurement is made of the mechanical resonance of the sensor membrane. This same measurement can be made at point after the sensor has been implanted. By comparing the values of these two measurements a determination of the degree of change in mechanical resonance frequency can be established. This value can then be used to create a calibration factor that can be applied to the pressure reading taken post-implantation in order to adjust the measured value to reflect the actual pressure within the heart chamber.

The preceding specific embodiments are illustrative of the practice of the invention. It is to be understood, however, that other expedients known to those skilled in the art or disclosed herein, may be employed without departing from the spirit of the invention of the scope of the appended claims.

We claim:

1. An apparatus comprising:
   an elongated catheter having proximal and distal ends and having a lumen extending therethrough, said lumen having a cross-sectional area;
   a push rod slidably disposed within said lumen of said catheter;
   said catheter and said push rod being arranged such that there is a recess formed at said distal end of said catheter; and
      a flexible sensor for wirelessly determining a physical property in a patient's heart chamber, which sensor comprises a self-contained resonant circuit a that is variable in response to said physical property, and said sensor being folded and received within said recess at said distal end of said catheter.

2. An apparatus comprising:
   an elongated catheter having proximal and distal ends and having a lumen extending therethrough, said lumen having a cross-sectional area;
   a push rod slidably disposed within said lumen of said catheter;
   said catheter and said push rod being arranged such that there is a recess formed at said distal end of said catheter; and
   a flexible sensor for wirelessly determining a physical property in a patient's heart chamber, which sensor comprises a self-contained resonant circuit comprising a capacitor and an inductor, wherein the circuit is variable in response to said physical property, wherein the capacitance of the capacitor is variable in response to the physical property of the patient, wherein the inductor is adapted to allow inductance of a current in the resonant circuit when the sensor is subjected to a time-varying electromagnetic field, and said sensor being folded and received within said recess at said distal end of said catheter.

3. An apparatus comprising:
   an elongated catheter having proximal and distal ends and having a lumen extending therethrough, said lumen having a cross-sectional area;
   a push rod slidably disposed within said lumen of said catheter;
   said catheter and said push rod being arranged such that there is a recess formed at said distal end of said catheter; and
   a flexible sensor for wirelessly determining a physical property in a patient's heart chamber, which sensor comprises a self-contained resonant circuit comprising a capacitor and an inductor, wherein the circuit is variable in response to the physical property of the patient, and wherein the sensor has an anchoring system attached to a flat surface of the sensor, and said sensor being folded and received within said recess at said distal end of said catheter.

4. The sensor of claim 3, wherein the capacitance of the capacitor is variable in response to the physical property of the patient.

5. The sensor of claim 3, wherein the inductor is adapted to allow inductance of a current in the resonant circuit when the sensor is subjected to a time-varying electromagnetic field.

6. The sensor of claim 3, wherein the physical property is pressure or temperature.

7. The sensor of claim 6, wherein the physical property is pressure.

8. The sensor of claim 3, wherein the sensor is disk-shaped.

9. The sensor of claim 8, wherein the sensor has one or more metallic members attached to a flat surface of the sensor.

10. The sensor of claim 8, wherein the sensor has one or more metallic members layered within the sensor.

11. The sensor of claim 8, wherein the sensor has a metallic ring surrounding a portion of the edge of the sensor.

12. The sensor of claim 3, wherein the sensor has a daisy or flower shape.

13. The sensor of claim 3 wherein the sensor has a shape so that portions of the sensor can be folded at an approximately 90° angle to a substantially flat middle section.

14. The sensor of claim 3, wherein the anchoring system is a coil.

15. The sensor of claim 3, wherein the anchoring system has a projection with umbrella-like radial projections.

16. The sensor of claim 3, wherein the sensor has one or more cut-outs to facilitate folding.

17. The sensor of claim 3, which can be folded into a U-shape.

18. The sensor of claim 3, wherein the primary material of construction is flexible, biocompatible polymer or co-polymer.

19. The sensor of claim 18, wherein the polymer or co-polymer is selected from the group consisting of polyamide, polyethylene teraphthalate, polytetrafluoroethlyene, and co-polymers thereof.

20. The sensor of claim 3, which contains a non-linear element and responds in a non-linear manner to an excitation signal.

21. The sensor of claim 3, wherein the capacitance is distributed across an array of smaller capacitors.

22. The sensor of claim 3, which can be folded so that a middle section remains substantially flat, the outer edges or surfaces are at substantially a 90° angle to said middle section, and a portion of the inductor is substantially coextensive with the outer edge.

23. The sensor of claim 22, which is substantially daisy-shaped.

24. A sensor comprising:
a first layer of material having an upper surface and a lower surface,
a first capacitor element disposed on a central portion of said lower surface of said first layer of material;
a first inductor element disposed on said lower surface of said first layer of material coplanar with said first capacitor element and electrically connected to said first capacitor element;
a second layer of material having an upper surface and a lower surface, said second layer of material being disposed in generally parallel, spaced-apart relation to said first layer of material with said lower surface of said first layer of material and said upper surface of said second layer of material being adjacent one another;
a second capacitor element disposed on a central portion of said upper surface of said second layer of material;
a second inductor element disposed on said upper surface of said second layer of material coplanar with said second capacitor element and electrically connected to said second capacitor element;
a third layer of material extending between said lower surface of said first layer of material and said upper surface of said second layer of material, said third layer of material being interposed between said first and second inductor elements, said third layer of material having an opening formed in a central portion thereof substantially in alignment with said first and second capacitor elements and maintaining said first and second capacitor elements in spaced-apart relation, said opening being dimensioned and configured such that said first and second capacitor elements are moveable toward and away from one another in response to changes in pressure against the upper surface of said first layer of material and the lower surface of said second layer of material;
said first and second capacitor elements forming a capacitor,
said first and second inductor elements forming an inductor,
said capacitor and inductor forming a self-contained resonant circuit, and
the capacitance of said resonant circuit being variable in response to changes in pressure in the surrounding environment.

25. The sensor of claim 24, wherein said first and second inductor elements comprise coils.

26. The sensor of claim 24,
wherein said first inductor element is substantially concentric with said first capacitor element, and
wherein said second inductor element is substantially concentric with said second capacitor element.

27. The sensor of claim 24, wherein said first and second capacitor elements comprise circular plates.

28. The sensor of claim 24, wherein said third layer of material comprises an adhesive that bonds said first layer of material to said second layer of material.

29. The sensor of claim 24, wherein said first and second inductor elements are embedded in said third material.

30. The sensor of claim 24, wherein the inductor is operative to allow inductance of a current in the resonant circuit when the sensor is subjected to a time-varying electromagnetic field.

31. The sensor of claim 24, wherein the material comprising said first and second layers is flexible, biocompatible polymer or co-polymer.

32. The sensor of claim 31, wherein the polymer or co-polymer is selected from the group consisting of polyamide, polyethylene teraphthalate, polytetrafluoroethlyene, and co-polymers thereof.

* * * * *